United States Patent
Campbell et al.

(10) Patent No.: US 6,680,068 B2
(45) Date of Patent: Jan. 20, 2004

(54) DRUG DELIVERY FORMULATIONS AND TARGETING

(75) Inventors: Robert B. Campbell, Boston, MA (US); Rakesh K. Jain, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/898,107

(22) Filed: Jul. 3, 2001

(65) Prior Publication Data

US 2002/0090392 A1 Jul. 11, 2002

Related U.S. Application Data

(60) Provisional application No. 60/216,173, filed on Jul. 1, 2000.

(51) Int. Cl.[7] .......................... A61K 9/127; A61K 48/00
(52) U.S. Cl. .............................. 424/450; 514/1; 514/2; 514/44
(58) Field of Search .............................. 424/450; 514/1, 514/2, 44

(56) References Cited

U.S. PATENT DOCUMENTS

| | | | |
|---|---|---|---|
| 4,804,539 A | 2/1989 | Guo et al. | 424/450 |
| 4,839,175 A | 6/1989 | Guo et al. | 424/450 |

OTHER PUBLICATIONS

Verma et al (Nature 389: 239–242, 1997).*
Somia and Verma (Nature Reviews Genetics 1: 91–99, 2000).*
Anderson (Nature 392:25–30, 1998).*
Romano et al (Stem Cells 18: 19–39, 2000).*
McCluskie et al (Molecular Medicine 5 (5): 287–300, 1999).*
Chattergoon et al (FASEB J. 11: 753–763, 1997).*
Irvine et al (J. Immunol. 156(1): 238–245, 1996).*
Baldwin et al., (1991) Microvascular Research 42:160–178.
Dellian et al., (2000) British Journal of Cancer 82:1513–1518.
Folkman, (1990) Journal of the National Cancer Institute 82(1):4–6.
Hobbs et al., (1998)Proc. Natl. Acad. Sci. USA 95:4607–4612.
Jain, (1998) Nature Medicine 6:655–657.
Jain, (1994) Scientific American 271 (1):58–65.
Roberts et al., (1997) Cancer Research 57:765–772.
Thurston et al., (1998) Journal of Clinical Investigation 101:1401–1413.

* cited by examiner

*Primary Examiner*—Dave T. Nguyen
*Assistant Examiner*—Richard Schnizer
(74) *Attorney, Agent, or Firm*—Fish & Richardson P.C.

(57) ABSTRACT

The invention is based on the discovery that angiogenic vessels have heterogeneous surface charge and that cationic liposomes actually target human tumor blood vessels only in irregularly shaped patches. The invention thus features methods for delivering therapeutic compounds to angiogenic vascular endothelial surfaces using a mixture, or "cocktail", of positively charged and neutral liposomes. The new methods can be used to target multiple regions on the same tumor vessel and/or clusters of vessels within the same tumor. Liposomes with different chemical and/or physical properties (e.g., charge, stability, solubility, diameter) can be delivered simultaneously, and can target tumor vessels and other angiogenic vessels with greater efficiency compared to cationic liposomes alone.

14 Claims, No Drawings

DRUG DELIVERY FORMULATIONS AND TARGETING

CROSS REFERENCE TO RELATED APPLICATIONS

This application claims the benefit of priority under 35 USC §119(e)(1) of Provisional Application No. 60/216,173 filed Jul. 6, 2000.

STATEMENT AS TO FEDERALLY SPONSORED RESEARCH

This invention was made with Government support under Outstanding Investigator Grant R35-CA-56591 awarded by the National Institutes of Health. The Government may have certain rights in the invention.

FIELD OF THE INVENTION

The invention relates to drug delivery.

BACKGROUND OF THE INVENTION

The efficiency of drug transport to solid tumors can vary as a function of host microenvironment, tumor type, and growth. Several barriers have been shown to impede delivery of therapeutics to solid tumors in clinically relevant concentrations (Jain, *Scientific American,* 271(1):58–65, 1994). These barriers include a heterogeneous blood supply, elevated tumor interstitial pressure (Jain, *Nature Medicine,* 6:655–657, 1998), and a dynamic range of tumor blood vessel pore sizes (Hobbs et al., *Proc. Natl. Acad. Sci. USA,* 95:4607–4612, 1998). Delivery of drugs to solid tumors can thus present a formidable challenge.

Studies have shown anatomical and morphological differences between normal and tumor blood vessels (Baldwin et al., *Microvascular Research,* 42:160–178, 1991). Most tumors are angiogenesis-dependent (Folkman, *Journal of the National Cancer Institute,* 82(1):4–6, 1989), requiring the development of new blood vessels. The glycoprotein layer of the vascular endothelium of angiogenic blood vessels is composed primarily of negatively charged functional groups (Baldwin et al., *Microvascular Research,* 42:160–178, 1991). These functional groups can facilitate molecular interactions with positively charged macromolecules (Dellian et al., *British Journal of Cancer,* 82:1513–1518, 2000). Accordingly, it was hypothesized that cationic liposomes could be used to target tumor vessels where established glycoprotein layers had formed. Indeed, it was found that cationic liposomes are taken up by tumor vessels to a greater extent than by the normal vascular endothelia. Cationic liposomes have thus been used to target anionic endothelial cells in tumors and chronic inflammation in mice, with some success (Thurston et al., *Journal of Clinical Investigation* 101:1401–1413, 1998; Roberts et al., *Cancer Research* 57:765–772, 1997).

In addition to tumor growth, numerous other disease states are associated with abnormal angiogenesis. Increased angiogenesis in the bones, joints, skin, liver, kidney, lung, ear, nerves, heart, skeletal muscles, adipose tissue, peritoneum pleura, endocrine organs, hematopoiesis, lymph, and other organs and systems, for example, is associated with tumors and chronic inflammation in those organs, as well as obesity, warts, uterine bleeding, and respiratory disease. On the other hand, vascular insufficiency is associated with diseases such as aseptic necrosis, impaired healing of fractures, decubitus or stasis ulcers, gastrointestinal ulcers, pulmonary and systemic hypertension, placental insufficiency, stroke, vascular dementia, Alzheimer's disease, CADASIL, ischemic heart and limb disease, and thyroid pseudocysts. Other vascular abnormalities have been implicated in psoriasis, diabetes, and hypertension.

SUMMARY OF THE INVENTION

The invention is based on the discovery that angiogenic vessels have heterogeneous surface charge and that cationic liposomes actually target human tumor blood vessels only in irregularly shaped patches. The invention thus features methods for delivering therapeutic compounds to angiogenic vascular endothelial surfaces using a mixture, or "cocktail", of positively charged and neutral liposomes. The new methods can be used to target multiple regions on the same tumor vessel and/or clusters of vessels within the same tumor. Liposomes with different chemical and/or physical properties (e.g., charge, stability, solubility, diameter) can be delivered simultaneously, and can target tumor vessels and other angiogenic vessels with greater efficiency compared to cationic liposomes alone.

In general, the invention features a formulation that includes cationic liposomes, containing a first therapeutic agent, and electrostatically neutral liposomes, containing a second therapeutic agent, where the first and second therapeutic agents can be the same or different. Each therapeutic agent can include, for example, one or more compound that have, or are suspected to have, some biological activity, as well as other additives and excipients. Preferably, such additives or excipients are substantially non-toxic at the concentration and quantity employed. The cationic and neutral liposomes can be present in various ratios (e.g., between about 1:9 and 9:1, between about 1:3 and 3:1, or between about 2:3 and 3:2, such as about 1:1. Either or both of the first and second therapeutic agents can be, for example, an anti-tumor drug (e.g., a chemotherapeutic agent such as paclitaxel, doxorubicin, or other plant alkaloids, antibiotics, alkylating agents, antimetabolites, or miscellaneous agents), a nucleic acid, or another natural or synthetic therapeutic agent. The cationic lipids can include, for example, dioleoyltrimethyl-ammonium propane (DOTAP), N-[1-(2,3-dioleoyloxy)-propyl]-N,N,N-trimethylammonium chloride (DOTMA), dimethyldioctadecylammonium bromide (DDAB), 1,2-dimyristyloxypropyl-3-dimethylhydroxyethyl (DMRIE), dioleoyl-3-dimethylammonium propane (DODAP), N,N-dioleyl-N,N-dimethylammonium chloride (DODAC), or N-(1-(2,3-dioleyloxy)propyl)-N-(2-(sperminecarboxamido)ethyl)-N,N-dimethyl ammonium trifluoroacetate (DOSPA), or any other natural or synthetic cationic lipids. The neutral liposomes can include, for example, dioleoylphosphatidylcholine (DOPC), dipalmitoylphosphatidylcholine (DPPC), disteroylphosphatidylcholine (DSPC), dimyristoylphosphatidylcholine (DMPC), or 1,2-sn-dioleoylphosphatidylcholine (DOPE), or any other natural or synthetic electrostatically neutral lipids.

The invention also features several methods of administering a drug to a patient. One method includes the steps of providing a formulation as described above (i.e., where at least one of the first and second therapeutic agents includes the drug to be administered), and administering the formulation to the patient (e.g., intravenously or intraarterially or by any other suitable route). The patient can be, for example, a patient suspected of having a tumor. The patient can be, for example, a mammal such as a human, a mouse, a rat, a sheep, a goat, a dog, a cat, a pig, a cow, or other animal used for research, human companionship, agriculture, or consumption. Another method includes administering to the patient a formulation that includes a heterogeneously charged drug delivery system that can include liposomes or other drug carriers. A third method includes administering to the patient two differently charged therapeutic formulations, either or both of which can include the drug.

The invention provides several advantages. Liposome formulations can function as vascular targeting systems. Several reasons currently exist for applying vascular targeting strategies. First, damage to even a single vessel can leaves hundreds or thousands of neoplastic cells starving for nutrients, resulting in the death of a significant number of malignant cells. The blood vessels carry nutrients to the cells; without the nutrients, the cells cannot survive. Second, the physical barriers that impede delivery of drugs to solid tumors do not provide an obstacle to drug delivery to the vascular endothelium. The new methods are also not limited to delivery of therapeutics to tumor interstitial space where the majority of tumor cells reside. Additionally, the vascular targeting agent can target both the tumor vascular endothelium and a percentage of tumor cells in the tumor interstitium, resulting in additional gains in therapy. Third, endothelial cells are generally non-malignant, although they can in some cases mutate as a tumor progresses. As a result, mutant phenotypes are rare, and drug resistance is unlikely to arise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The new formulations and methods provide improved vascular targeting of drugs to solid tumors. Liposomes that include PEG lipids conjugated to phospholipid surfaces can enhance systemic circulation, reduce side effects (e.g., nausea, vomiting, headache, leukopenia), and to improve the general therapeutic dose.

We have discovered that the charge lining the vascular endothelium of tumor vessels is heterogeneous, and that overall vascular targeting efficiency can be improved by intravenously injecting a mixture of cationic and neutral liposomes simultaneously. We have found that this method enhances uptake of liposomes. Tumor charge heterogeneity can thus be exploited to optimally deliver therapeutics to blood vessels of solid tumors. The new formulations and methods thus improve delivery of drugs, for example, to the vasculature of solid tumors and angiogenic tissue, and increase the probability of tumor cell death. Moreover, while cationic liposomes target the vascular surface, electrostatically neutral liposomes can associate with the vascular wall. Due to large tumor vascular pore sizes, they also have the ability to extravasate into tumoral tissues over time. Hence, although the normal vasculature may take up some of the drug carried by the neutral liposomes, the total accumulation in tumors is still greater.

Liposome Formulations

The new formulations generally include both cationic liposomes and electrostatically neutral liposomes.

The ratio of cationic liposomes to neutral liposomes will depend on the desired overall percent charge. The optimal percent charge for a particular tumor type can be determined by preparing a series of formulations with different percent charges (e.g., from 0% to about 50%), then determining which formulation best targets the tumor vasculature. Targeting can be quantified by intravital microscopy of cationic liposomes at the tumor vascular surface in vivo, according to the methods used in Fan Yuan et al. (*Cancer Research*, 54:3352–3356, 1994) to study microvascular permeability and interstitial penetration of sterically stabilized ("stealth") liposomes in a human tumor xenograft.

The half-life of the new liposome formulations in blood varies as a function of percent charge. Plasma clearance curves associated with the new formulations indicate that high percent charge liposomal formulations clear faster than lower percent charged formulations do. Optionally, circulation times be extended by temporarily blocking the reticuloendothelial system (RES), which can function to eliminate liposomes from systemic circulation.

In general, the liposomes are prepared as follows: A desired phospholipid composition is selected for use in making the liposomes. The selected lipids can be freeze-dried or lyophilized (e.g., to enhance lipid packing and/or eliminate trace amounts of organic solvents). An optimal number of phospholipid head groups are exposed for efficient hydration in a desired buffer (e.g., 50:50 saline/distilled water, 308 mM NaCl, or 40 mM Hepes; pH 7.4) to form liposomes of acceptable grade. The liposomes can be fixed to a specific size by using an extruder that contains special membranes containing fixed pore sizes (e.g., 100 nm). The cationic and neutral liposomes are then combined to yield a desired ratio (e.g., from about 1:9 to about 9:1, e.g., about 3:2 to about 2:3).

The neutral liposomes can be prepared, for example, from dioleoylphosphatidyl-choline (DOPC), cholesterol (CHOL), and polyethylene glycol (PEG) in various ratios (e.g., 50:45:5). Other electrostatically neutral phospholipids (e.g., dipalmitoylphosphatidylcholine (DPPC), disteroylphosphatidylcholine (DSPC), dimyristoylphosphatidylcholine (DMPC), or 1,2-sn-dioleoylphosphatidylcholine (DOPE), or other synthetic or naturally occurring electrostatically neutral lipids) can be substituted for DOPC. These and other components can be purchased, for example, from Avanti Polar Lipids, Inc. (Alabaster, Ala.).

The cationic liposomes can be prepared from DOPC, CHOL, dioleoyltrimethyl-ammonium propane (DOTAP), and PEG in various ratios (e.g., 35:10:50:5 or 45:10:40:5), to yield a desired net positive charge (defined as mole fraction of cationic lipids divided by mole fraction of all lipids in the cationic liposome) at physiological pH (e.g., pH 7.4). DOTAP has low toxicity in vivo, but other cationic lipids (e.g., N-[1-(2,3-dioleoyloxy)-propyl]-N,N,N-trimethylammonium chloride (DOTMA), dimethyldioctadecylammonium bromide (DDAB), 1,2-dimyristyloxypropyl-3-dimethylhydroxyethyl (DMRIE), dioleoyl-3-dimethylammonium propane (DODAP), N,N-dioleyl-N,N-dimethylammonium chloride, (DODAC), N-(1-(2,3-dioleyloxy)propyl)-N-(2-(sperminecarboxamido)ethyl)-N,N-dimethyl ammonium trifluoroacetate (DOSPA), or other synthetic or naturally occurring cationic lipids) can be used in its place.

The size of the liposomes can also affect selectivity. Prolonged circulation time of liposomes enhances target binding and retention of liposomes. Relatively small liposomes (e.g., 200 nm or smaller) circulate longer than large liposomes (e.g., 500 nm or larger). Moreover, incorporation of polyethylene glycol derivatized with phosphatidyl ethanolamine (PEG-PE) into the formulations of the individual liposomes can prolong circulation time, possibly by providing a steric barrier that prevents close contact with other liposomes or cells. Cationic liposomes without PEG are taken up by the reticuloendothelial system (RES) at a much higher rate than PEGylated cationic liposomes are.

Drugs for Incorporation into Liposome Cocktails

Both hydrophobic and water-soluble drugs can be incorporated or encapsulated in the new formulations. Paclitaxel, a chemotherapeutic drug used to treat solid malignancies such as breast, ovarian, head, and neck cancer, for example, can be stably incorporated into a liposome cocktail. Similarly, doxorubicin can be incorporated into the new liposome cocktails to achieve better vascular targeting than that observed with standard doxorubicin/liposome preparations such as DOXIL®. Other chemotherapeutic agents such as alkylating agents (e.g., mechlorethamine hydrochloride, cyclophosphamide, ifosfamide, chlorambucil, melphalan, busulfan, thiotepa, carmustine, lomustine, streptozocin), plant alkaloids (e.g., vincristine, vinblastine, vinorelbine, docetaxel), antimetabolites (e.g., methotrexate, mercaptopurine, thioguanine, fluorouracil, cytarabine, azacitidine, fludarabine, cladribine, pentostatin), antibiotics (e.g., dactinomycin, daunorubicin, idarubicin, mitoxantrone, bleomycin, plicamycin, mitomycin), or miscellaneous agents (e.g., hydroxyurea, procarbazine, dacarbazine, cisplatin, carboplatin, asparaginase, etoposide, amsacrine, mitotane, topotecan, tretinoin) can also be incorporated into the cocktails, either alone or in combination, as can other natural or synthetic therapeutic agents such as those listed in the Merck Manual and/or the Merck Index, both of which are incorporated by reference.

Nucleic acids such as DNA can also be incorporated into the new liposome cocktails (e.g., for gene therapy applications and for delivery of immunostimulatory agents such as poly I:C). The positively charged lipids of the cationic liposomes can form an electrostatic complex with the phosphate backbone of the DNA. This interaction can facilitate delivery and uptake of DNA by cells.

Methods of Treatment Using Liposome Cocktails

The binding of cationic liposomes to tumor vascular endothelium is heterogeneous. The liposome formulations of the invention accordingly provide a new approach to the delivery of clinically relevant concentrations of drugs to tumors. Liposome formulations containing only cationic liposomes lack the ability to target the heterogeneous tissue as thoroughly as the new formulations do. The new formulations can also include liposomes varying in pharmacokinetic profiles. For example, charge appears to regulate liposome plasma clearance rates.

PEGylated cationic liposomes (including 5 mol % PEG) having 10% or 20% net positive charge clear the blood at a rate much slower than that of PEGylated cationic liposomes containing 40% or 50% net positive charges. Liposomes having such different plasma clearance rates can be used together to enhance therapy. In addition, electrostatically neutral liposomes have a plasma clearance kinetic profile completely different from that of charged liposomes, and thus further regulate the clearance profile of a given liposome cocktail of the invention. The combination of liposomes having different surface charges and plasma clearance rates can be advantageous for cancer therapy, since one type of liposome may work immediately, while another remains in circulation, available to target the tumor at a later point in time.

EXAMPLES

The invention is further described in the following examples, which do not limit the scope of the invention described in the claims.

Example 1

Preparation of Liposome Cocktails

Both cationic liposomes and electrostatically neutral liposomes were separately prepared by dissolving each individual lipid component in chloroform to a concentration of 10 mM. Aliquots of each component were transferred to round bottom flasks using a glass syringe, to provide 35:10:50:5 and 45:10:40:5 ratios of DOPC:CHOL:DOTAP:PEG for two formulations of cationic liposomes, and a 50:45:5 ratio of DOPC:CHOL:PEG for the neutral liposomes. Rhodamine-labeled phospholipids were then added so that post-injection liposome uptake could be detected. The chloroform was then evaporated with adequate ventilation under an inert gas stream, resulting in a lipid film. The flask was attached to a vacuum pump for 10 to 15 minutes, after which time the lipid film was immediately suspended in a 50:50 mixture of physiological saline and distilled water. The liposomes formed in the aqueous solution were then passed through 200 mu filters (Whatman) to sterilize the preparations. Next, the formulations were passed through an Avanti microextruder with a 100 nm filter membrane (Whatman). The cationic and neutral liposomes were then combined in a 50:50 ratio to yield the desired charge ratio. Prior to injection into tumor-bearing mice, the resulting liposome formulation was warmed to 37° C.

Example 2

Injection of a Liposome Cocktail

LS174T human colon adenocarcinoma cells and B16F10 murine melanoma cells were grown in dorsal skin fold chambers in Rag2 −/− mice. In vivo microscopy was performed using a microscope with epi-illumination. All vessels used in permeability studies were well perfused. Fluorescently labeled PEGylated and non-PEGylated cationic liposomes (100 nm) were prepared according to the method of Yuan et al. (Cancer Research, 55:3752–3756, 1995).

Dextran (mol. wt ~2,000,000) labeled with the fluorescent tracer FITC (Sigma, St. Louis, Mo.) was used to visualize blood vessels. The FITC-dextran was injected intravenously into the tail vein of a B16F10 tumor-bearing mouse. The blood flow to the tumor vessels was confirmed to have been functional before injection of liposomes.

Using the same experimental conditions as in the above tracer experiment, rhodamine-labeled, PEGylated cationic liposomes with a 50% charge were injected into a B16F10 tumor-bearing mouse. Regions of high liposome uptake were observed, as well as some regions of poor liposome uptake. Not all well perfused areas of B16F10 melanoma tumor vessels showed preferential uptake of cationic liposomes, indicating, unexpectedly, that the response of tumors to charge is heterogeneous. Experiments with MCAIV (a murine breast tumor) and LS174T (a human adenocarcinoma of the colon) yielded similar results.

The qualitative experiments indicated that LS174T human adenocarcinoma tumors and B16F10 melanoma tumors preferentially take up cationic liposomes, compared with past experiments with anionic and electrostatically neutral liposomes, and greater vascular targeting of B16F10 vessels (n=3) was observed at higher cationic lipid ratios (>30% DOTAP). Furthermore, vascular targeting of PEGylated cationic liposomes appeared to be a random process with some vessels targeted to a greater extent than others.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A formulation comprising:
   cationic liposomes comprising a first therapeutic agent, and
   electrostatically neutral liposomes comprising a second therapeutic agent,
   wherein the first and second therapeutic agents can be the same or different.

2. The formulation of claim 1, wherein the ratio of cationic liposomes to neutral liposomes is between 1:9 and 9:1.

3. The formulation of claim 1, wherein the ratio of cationic liposomes to neutral liposomes is between 1:3 and 3:1.

4. The formulation of claim 1, wherein the ratio of cationic liposomes to neutral liposomes is between 2:3 and 3:2.

5. The formulation of claim 1, wherein at least one of the first and second therapeutic agents is an anti-tumor drug.

6. The formulation of claim 1, wherein at least one of the first and second therapeutic agents is a nucleic acid.

7. The formulation of claim 1, wherein the cationic liposomes comprise one or more lipids selected from the group consisting of dioleoyltrimethyl-ammonium propane (DOTAP), N-[1-(2,3-dioleoyloxy)-propyl]-N,N,N-triethylammonium chloride (DOTMA), dimethyldioctadecylammonium bromide (DDAB), 1,2-dimyristyloxypropyl-3-dimethylhydroxyethyl (DMRIE), dioleoyl-3-dimethylammonium propane (DODAP), N,N-dioleyl-N,N-dimethylammonium chloride (DODAC), and N-(1-(2,3-dioleyloxy)-propyl)-N-(2-(sperminecarboxamido)ethyl)-N,N-dimethyl ammonium trifluoroacetate (DOSPA).

8. The formulation of claim 1, wherein at least one of the first and second therapeutic agents is selected from the group consisting of alkylating agents, plant alkaloids, antimetabolites, and antibiotic.

9. The formulation of claim 1, wherein the neutral liposomes comprise one or more lipids selected from the group consisting of dioleoylphosphatidyl-choline (DOPC), dipalmitoylphosphatidylcholine (DPPC), disteroylphosphatidylcholine (DSPC), dimyristoylphosphatidylcholine (DMPC), and 1,2-sn-dioleoylphosphatidylcholine (DOPE).

10. The formulation of claim 1, wherein at least one of the first and second therapeutic agents is selected from the group consisting of mechlorethamine hydrochloride, cyclophosphamide, ifosfamide, chlorambucil, melphalan, busulfan, thiotepa, carmustine, lomustine, and streptozocin.

11. The formulation of claim 1, wherein at least one of the first and second therapeutic agents is selected from the group consisting of vincristine, paclitaxel, vinblastine, vinorelbine, and docetaxel.

12. A The formulation of claim 1, wherein at least one of the first and second therapeutic agents is selected from the group consisting of methotrexate, mercaptopurine, thioguanine, fluorouracil, cytarabine, azacitidine, fludarabine, cladribine, and pentostatin.

13. The formulation of claim 1, wherein at least one of the first and second therapeutic agents is selected from the group consisting of dactinomycin, daunorubicin, doxorubicin, idarubicin, mitoxantrone, bleomycin, plicamycin, and mitomycin.

14. The formulation of claim 1, wherein at least one of the first and second therapeutic agents is selected from the group consisting of hydroxyurea, procarbazine, dacarbazine, cisplatin, carboplatin, asparaginase, etoposide, amsacrine, mitotane, topotecan, and tretinoin.

* * * * *